(12) United States Patent
Henderson

(10) Patent No.: US 7,318,838 B2
(45) Date of Patent: Jan. 15, 2008

(54) SMART TEXTILE VASCULAR GRAFT

(75) Inventor: Jamie Henderson, Oakland, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 406 days.

(21) Appl. No.: 11/026,658

(22) Filed: Dec. 31, 2004

(65) Prior Publication Data

US 2006/0147487 A1 Jul. 6, 2006

(51) Int. Cl. *A61F 2/06* (2006.01)
(52) U.S. Cl. ............ 623/1.34; 623/1.54; 600/505; 600/486
(58) Field of Classification Search ...... 623/1.11–1.54; 606/505, 486
See application file for complete search history.

(56) References Cited

U.S. PATENT DOCUMENTS

| | | | |
|---|---|---|---|
| 4,738,740 A | 4/1988 | Pinchuk et al. |
| 4,990,158 A | 2/1991 | Kaplan et al. |
| 4,997,440 A | 3/1991 | Dumican |
| 5,116,360 A | 5/1992 | Pinchuk et al. |
| 5,127,919 A | 7/1992 | Ibrahim et al. |
| 5,163,951 A | 11/1992 | Pinchuk et al. |
| 5,366,504 A | 11/1994 | Andersen et al. |
| 5,612,885 A | 3/1997 | Love |
| 5,732,572 A | 3/1998 | Litton |
| 5,843,158 A | 12/1998 | Lenker et al. |
| 5,967,986 A | 10/1999 | Cimochowski et al. |
| 6,042,605 A | 3/2000 | Martin et al. |
| 6,136,022 A | 10/2000 | Nunez et al. |
| 6,159,156 A | 12/2000 | Van Bockel |
| 6,164,339 A | 12/2000 | Greenhalgh |
| 6,176,871 B1 | 1/2001 | Pathak et al. |
| 6,454,796 B1 | 9/2002 | Barkman et al. |
| 6,540,773 B2 | 4/2003 | Dong |
| 6,554,855 B1 | 4/2003 | Dong |
| 6,652,570 B2 | 11/2003 | Smith et al. |
| 6,733,522 B2 | 5/2004 | Schmitt et al. |
| 6,814,753 B2 | 11/2004 | Schmitt |
| 6,840,956 B1 * | 1/2005 | Wolinsky et al. ......... 623/1.13 |
| 2003/0069475 A1 | 4/2003 | Banik et al. |
| 2003/0212306 A1 | 11/2003 | Banik |
| 2003/0236531 A1 | 12/2003 | Couvillon, Jr. |
| 2004/0068161 A1 | 4/2004 | Couvillon, Jr. |
| 2004/0068220 A1 | 4/2004 | Couvillon, Jr. et al. |

(Continued)

FOREIGN PATENT DOCUMENTS

WO WO03/002036 1/2003

OTHER PUBLICATIONS

"Sensatex SmartShirt™", *Sensatex* (1 page) (http://www.sensatex.com/index.html).

*Primary Examiner*—Suzette Gherbi
(74) *Attorney, Agent, or Firm*—Hoffmann & Baron, LLP (57) ABSTRACT

The smart textile vascular graft is used with an electrical control unit. The vascular graft includes a tube structure formed of a textile material. At least one active fiber is incorporated in the textile material. The active fiber provides electrical coupling thereof to the electrical control unit to provide for transmission of a control signal between the active fiber and control unit. The active fiber has at least one physical characteristic which is variable and corresponds to the control signal to provide communication between the active fiber and electrical control unit relating to the physical characteristic.

23 Claims, 1 Drawing Sheet

U.S. PATENT DOCUMENTS

| | | |
|---|---|---|
| 2004/0068224 A1 | 4/2004 | Couvillon, Jr. et al. |
| 2004/0073278 A1* | 4/2004 | Pachys ........................ 607/88 |
| 2004/0087982 A1 | 5/2004 | Eskuri |
| 2004/0098093 A1* | 5/2004 | DiCarlo ..................... 623/1.13 |
| 2004/0176672 A1* | 9/2004 | Silver et al. ................. 600/345 |
| 2004/0199238 A1* | 10/2004 | Brown et al ................. 623/1.1 |
| 2005/0080346 A1* | 4/2005 | Gianchandani et al. ..... 600/486 |
| 2006/0129050 A1* | 6/2006 | Martinson et al. .......... 600/505 |

* cited by examiner

SMART TEXTILE VASCULAR GRAFT

FIELD OF THE INVENTION

The present invention relates to a smart textile vascular graft and, more specifically, to a vascular graft having at least one active fiber which provides for monitoring, locating or changing the shape of the vascular graft within the body of a patient.

BACKGROUND OF THE INVENTION

Implantable vascular grafts are used in medical applications for the treatment of diseased or damaged blood vessels, such as arteries and veins. Such treatment may be necessitated by conditions in the arteries and veins, such as a stenosis, thrombosis, occlusion or aneurysm. A vascular graft may be used to repair, replace, or otherwise correct a diseased or damaged blood vessel.

A vascular graft may be a tubular prosthesis for replacement or repair of a damaged or diseased blood vessel. A vascular graft may be used in the vascular system, urogenital tract and bile duct, as well as in a variety of other applications in the body. A vascular graft may be reinforced to open and support various lumens in the body. Such a vascular graft may be used for the treatment of stenosis, strictures and aneurysms in blood vessels, such as arteries and veins. Such treatments include implanting the vascular graft within the blood vessel to open and/or reinforce collapsing or partially occluded sections of the vessel.

When a vascular graft is inserted into the body of a patient, monitoring of the environmental conditions of which the graft is subjected, such as temperature and pressure, typically becomes more difficult. Also, the location of specific portions of the vascular graft, such as the distal end thereof, within the body may be difficult, particularly as increased lengths of the graft are inserted into the body.

Additionally, physical characteristics of the vascular graft which facilitate insertion of the vascular graft into the body of a patient may be less desirable after the vascular graft has reached the desired destination within the body. For example, a low profile of the vascular graft is typically preferred for insertion of the graft into the body. However, a larger profile is frequently preferred for use within the body after the vascular graft is fully inserted therein. Also, manipulation from outside the body of portions of the vascular graft which are within the body is typically desired. Such manipulation may provide for the bending or changing of the physical hardness of portions of the vascular graft which are within the body.

SUMMARY OF THE INVENTION

The smart textile vascular graft of the present invention is used with an electrical control unit. The vascular graft includes a tube structure formed of a textile material. At least one active fiber is incorporated in the textile material. The active fiber provides electrical coupling thereof to the electrical control unit to provide for transmission of a control signal between the active fiber and control unit. The active fiber has at least one physical characteristic which is variable and corresponds to the control signal to provide communication between the active fiber and electrical control unit relating to the physical characteristic.

The communication between the active fiber and the electrical control unit provides for the monitoring or control of at least one physical characteristic of the active fiber. The incorporation of the active fiber in the tube structure provides for the physical characteristic of the active fiber to be representative of the corresponding physical characteristic of the portion of the vascular graft which adjoins the active fiber. Accordingly, the incorporation of the active fiber in the tube structure provides for the monitoring of blood pressure, heartbeat, temperature and indicate when the active fiber and the adjoining portion of the vascular graft is damaged or worn. Also, the incorporation of the active fiber in the tube structure may provide for the control of at least one physical characteristic thereof.

The physical characteristics which may be monitored include the temperature and pressure to which the active fiber and adjoining portion of the tube structure is subjected. The pressure may be determined by monitoring any physical deformation of the tube structure, which may be provided by incorporating a strain gauge in the active fiber.

Another physical characteristic which may be measured is the degree of transmission of a control signal through the active fiber. This measurement may be used to determine the location of the active fiber within the body of the patient which may indicate the location of the portion of the tube structure in which the active fiber is incorporated.

Also, one or more physical characteristics of the active fiber may be altered by receipt thereof of a specific control signal from the control unit. One such characteristic is the physical hardness of the active fiber. Changes in the physical hardness of the active fiber may produce corresponding changes in the physical hardness of the portion of the tube structure which adjoins the active fiber.

Another physical characteristic of the active fiber which may be altered by receipt thereof of a specific control signal from the control unit is the shape of the active fiber. Such a change in the shape of the active fiber produces a corresponding shape in the portion of the tube structure in which the active fiber is incorporated. This provides for controlled manipulation of the active fiber and adjoining portion of the tube structure in vivo. As used herein, "in vivo" means the tube structure and the one or more active fibers incorporated therein which have been inserted into the body of a patient. Such manipulation may produce changes in the rigidity of the active fiber and portion of the tube structure in which the active fiber is incorporated. The incorporation of one or more of such active fibers in the tube structure corresponds in many respects to an artificial muscle which may be controllably constricted or expanded.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
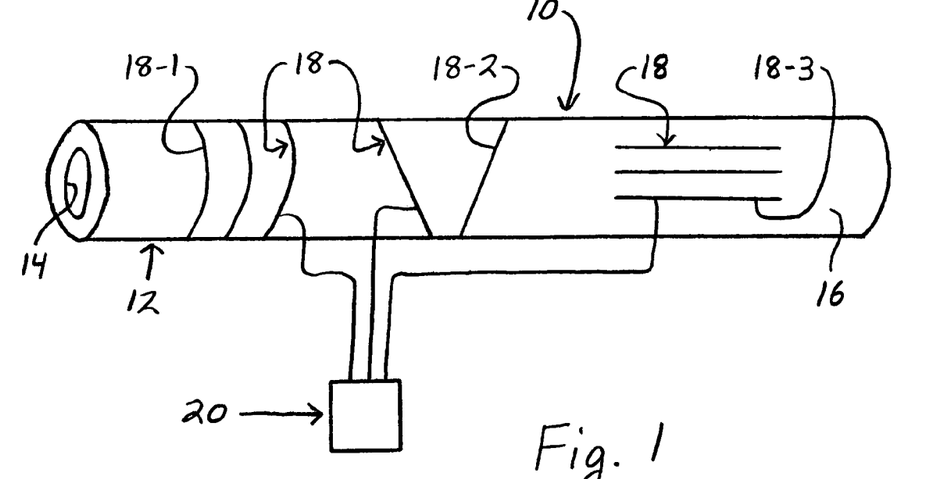
FIG. 1 is a side elevation view in schematic of a smart textile vascular graft of the present invention, the graft being shown as having active fibers which are electrically coupled to an electrical control unit.

Referring to the drawings and more particularly to FIG. 1, a smart textile vascular graft 10 is shown as including a tube structure 12 having inner and outer surfaces 14, 16. The tube structure 12 is a textile material, the threads or strands of which may be formed of polytetrafluoroethylene (PTFE) material, or polyester material.

The vascular graft 10 has at least one active fiber designated generally by 18 which is incorporated in the textile material of the tube structure 12. The incorporation may be provided by various techniques such as by weaving, knitting or braiding the active fiber 18 in the textile of the tube structure. More than one active fiber 18 may be incorporated in the tube structure 12.

The active fiber 18 is electrically coupled to an electrical control unit 20 preferably by a wireless system which may include a control unit 20 having an antenna for communication with the active fiber. Alternatively, the electrical coupling between the active fiber 18 and control unit may be provided by a radio signal or a hard-wire connection between the active fiber and control unit. Also, fiber optics may provide the coupling between the active fiber 18 and control unit. The electrical coupling provides for the transmission of a control signal between the active fiber 18 and control unit 20 in vivo. As used herein, "in vivo" means the tube structure 12 and the one or more active fibers 18 incorporated therein which have been inserted into the body of a patient. Also, it is possible for the control unit to be inserted into the body of the patient, such as by the control unit being mounted on a portion of the tube structure 12 or other implant which is inserted into the patient's body.

The active fiber 18 has at least one physical characteristic which is variable and corresponds to the control signal. This correspondence may result from the active fiber 18 being an electroactive polymer (EAP). Also, the active fiber 18 may be included in an electrical circuit which is incorporated in the textile material of the tube structure 12 such as by weaving, knitting or braiding the circuit therein. The resistance of the electrical circuit may correspond to the physical characteristic of the active fiber 18 to provide the correspondence between the physical characteristic and control signal. This provides communication between the active fiber 18 and control unit 20 relating to the physical characteristic. This communication may be continuous as provided by the continuous correspondence between the physical characteristic and control signal, and the continuous transmission of the control signal between the active fiber 18 and control unit 20.

Various physical characteristics of the active fiber 18 may be variable and correspond to the control signal. For example, the physical characteristic may be the temperature of the active fiber 18. Such an active fiber 18 provides a control signal which indicates the temperature of the active fiber for transmission to the control unit 20. To provide a control signal indicative of the temperature, the active fiber 18 may have a thermocouple. The incorporation of the active fiber 18 in the textile material of the tube structure 12 provides for thermal conductivity between the active fiber and the portion of the tube structure which adjoins the active fiber. Consequently, the temperature of the active fiber 18 indicated by the control signal corresponds to, and is preferably the same as, the temperature of the adjoining portion of the tube structure 12.

The incorporation of the active fiber 18 in the tube structure 12 may provide for the active fiber to be on the inner surface 14 such that the active fiber is exposed to the interior of the tube structure. Consequently, the control signal generated by the active fiber 18 provides an indication of the temperature within the tube structure 12. Alternatively, the incorporation of the active fiber 18 in the tube structure 12 may provide for the active fiber to be on the outer surface 16 such that the active fiber is exposed to the exterior of the tube structure. Consequently, the control signal generated by the active fiber 18 provides an indication of the temperature outside of the tube structure 12. Also, the active fiber 18 may extend through the textile material of the tube structure 12 to both the inner and outer surfaces 14, 16 such that portions of the active fiber are exposed to both the interior and exterior of the tube structure. Consequently, the control signal generated by the active fiber 18 provides an indication of the temperature both within and outside of the tube structure 12.

The transmission of the control signal to the control unit 20 may be initiated by the active fiber 18, or be responsive to a signal received by the active fiber from the control unit intended to prompt the transmission of the control signal by the active fiber to the control unit. The electrical coupling between the active fiber 18 and control unit 20 may provide for the continuous monitoring of the temperature of the active fiber and the adjoining portion of the tube structure 12.

In an alternative embodiment of the vascular graft 10, the physical characteristic of the active fiber 18 which corresponds to the control signal is the response of the active fiber to the pressure of the fluid or gas which is in direct contact with the active fiber. Consequently, the control signal generated by the active fiber 18 is indicative of the response of the active fiber which is indicative of the pressure of the fluid or gas to which the active fiber is exposed. Such an active fiber 18 may have a pressure transducer incorporated therein. The incorporation of the active fiber 18 in the tube structure 12 may provide for the active fiber to be on the inner surface 14 such that the active fiber is exposed to the interior of the tube structure. Consequently, the control signal generated by the active fiber 18 provides an indication of the pressure within the tube structure 12. The pressure within a tube structure 12 which carries blood is normally the blood pressure. Consequently, an active fiber 18 which indicates the pressure within such a tube structure 12 provides an indication of the blood pressure and heartbeat. Alternatively, the incorporation of the active fiber 18 in the tube structure 12 may provide for the active fiber to be on the outer surface 16 such that the active fiber is exposed to the exterior of the tube structure. Consequently, the control signal generated by the active fiber 18 provides an indication of the pressure outside of the tube structure 12. Also, the active fiber 18 may extend through the textile material of the tube structure 12 to both the inner and outer surfaces 14, 16 such that portions of the active fiber are exposed to both the interior and exterior of the tube structure. Consequently, the control signal generated by the active fiber 18 provides an indication of the pressure both within and outside of the tube structure 12.

The transmission of the control signal to the control unit 20 may be initiated by the active fiber 18, or be responsive to a signal received by the active fiber from the control unit intended to prompt the transmission of the control signal by the active fiber to the control unit. The electrical coupling between the active fiber 18 and control unit 20 may provide for the continuous monitoring of the pressure measured by the active fiber.

In an alternative embodiment of the vascular graft 10, the physical characteristic of the active fiber 18 which corresponds to the control signal is the longitudinal dimension of at least a portion of the active fiber. Such an active fiber 18 may have a strain gauge to indicate the dimension. The incorporation of the active fiber 18 in the textile material of the tube structure 12 provides for the anchoring of the active fiber to the portion of the tube structure which adjoins the active fiber such that the longitudinal dimension of the active fiber corresponds to the dimension of the adjoining portion of the tube structure. Consequently, the longitudinal dimension of the active fiber 18 indicated by the control signal is approximately the same as the dimension of the adjoining portion of the tube structure 12.

The transmission of the control signal to the control unit 20 may be initiated by the active fiber 18, or be responsive to a signal received by the active fiber from the control unit intended to prompt the transmission of the control signal from the active fiber to the control unit. The electrical coupling between the active fiber 18 and control unit 20 may provide for the continuous monitoring of the longitudinal dimension of the active fiber 18 and the dimension of the adjoining portion of the tube structure 12.

The continuous monitoring of the longitudinal dimension of the active fiber 18 and the dimension of the adjoining portion of the tube structure 12 may provide for the detection of an aneurysm in the tube structure 12 which normally characterized by a bulging thereof. Such a bulging produces an increase in the dimension of the tube structure 12 which is detected by the active fiber 18 assuming it or the adjoining portion of the tube structure are included in the portion of the tube structure distended by the aneurysm.

The monitoring of the longitudinal dimension of the active fiber 18 and the dimension of the adjoining portion of the tube structure 12 may provide an indication of the pressures to which the tube structure is subjected and the resulting stresses therein. For example, the longitudinal dimension of the active fiber 18 may indicate a pressure gradient between the inner and outer surfaces 14, 16. Such a gradient may result from the pressure within the tube structure 12 being greater than the pressure on the outer surface 16. Such a gradient, if sufficiently large, will normally cause the tube structure 12 to expand transversely resulting in a radial deformation and an increase in the transverse dimension of the tube structure. This increase in the transverse dimension will be measured by an active fiber 18-1 contained in a transverse plane of the tube structure 12, as shown in FIG. 1. Such a transverse plane will contain the active fiber 18-1 which encircles all or a portion of the tube structure 12 in a transverse orientation relative thereto. Such radial deformation may also be measured by an active fiber 18-2 having an inclined relation to the transverse plane, as shown in FIG. 1. Consequently, the active fibers 18-1, 18-2, by providing measurements of the longitudinal dimensions thereof and the dimensions of the adjoining portions of the tube structure 12, may provide indications of an increase in the pressure within the tube structure 12.

The pressure gradient between the inner and outer surfaces 14, 16 may change as a result of a decrease in the pressure within the tube structure 12. Such a decrease may result in a transverse deformation and a decrease in the transverse dimension of the tube structure 12. Such a decrease in the pressure within the tube structure 12 may result from a rupture in the tube structure which may be in close proximity to the active fibers 18-1, 18-2 or remote relative thereto. Consequently, the active fibers 18-1, 18-2, by providing measurements of the longitudinal dimensions thereof and the dimensions of the adjoining portions of the tube structure 12, may provide indications of a decrease in the pressure therein, which may be indicative a rupture in the tube structure.

An active fiber 18-3 having a longitudinal orientation relative to the tube structure 12 may provide a measurement of the longitudinal dimension of the adjoining portion of the tube structure 12. An increase in such longitudinal dimension normally results from a longitudinal tensile force applied to the tube structure 12 which produces a corresponding increase in the stress therein. Consequently, the active fiber 18-3, by providing measurements of the longitudinal dimension thereof and the adjoining portion of the tube structure 12, may provide indications of the longitudinal tension applied thereto and the resulting stress therein. A decrease in the longitudinal dimension of the active fiber 18-3 and the adjoining portion of the tube structure 12 may result from a decrease in a tensile force to which the active fiber and the adjoining portion of the tube structure may be subjected. Also, a decrease in the longitudinal dimension of the active fiber 18-3 and the adjoining portion of the tube structure 12 may result from the contraction or tensing of a muscle in which the active fiber and the adjoining portion of the tube structure are implanted.

In an alternative embodiment of the vascular graft 10, the physical characteristic of the active fiber 18 which corresponds to the control signal is the physical hardness of at least a portion of the active fiber. The physical hardness of such an active fiber 18 may be controllably changed by transmitting a specific control signal from the control unit 20 to the active fiber. The hardness of one or more of the active fibers 18 may affect the hardness of the tube structure 12 if a sufficient number of active fibers are incorporated in the textile material of the tube structure. Also, the correspondence between the respective hardness of the active fibers 18 and tube structure 12 may be made closer by effectively dispersing the active fibers throughout the tube structure, and weaving, braiding or knitting the active fibers in the textile material of the tube structure.

Increasing the hardness of the vascular graft 10 in vivo is desirable because the tube structure 12 and active fibers 18, or at least portions thereof, may preferably be in a relatively soft condition during insertion thereof into the body. In a preferred embodiment, a soft condition of the tube structure 12 and active fibers 18 during insertion thereof into the body provides for bending thereof which facilitates conformance of the vascular graft 10 with the lumen of the body through which the graft is inserted. However, in this embodiment, after the vascular graft 10 has reached the destination thereof in the body of the patient, an increased hardness of the tube structure 12 and active fibers 18 may be advantageous by providing a stent to the tube structure. Such a stent is advantageous because the increased hardness of the active fibers 18 and tube structure 12 resists expansion thereof which may result from an elevated pressure of the gas or fluid, which may be blood, within the tube structure. Also, the increased hardness may reduce the likelihood of a localized distension of the tube structure 12 and active fibers 18, such as an aneurysm or a puncture of the tube structure, in vivo. Such an increased hardness may be provided by transmitting the proper control signal from the control unit 20 to a sufficient number of active fibers 18 incorporated in the tube structure 12. The electrical coupling between the active fiber 18 and control unit 20 may provide for the continuous adjustment of the physical hardness of the active fibers 18 and the adjoining portions of the tube structure 12.

In an alternative embodiment of the vascular graft 10, the physical characteristic of the active fiber 18 which corresponds to the control signal is the shape of at least a portion of the active fiber. Such an active fiber 18 may be made from a polymer which significantly changes shape when a small electrical current is applied to the polymer. The shape of such an active fiber 18 may be controllably changed by transmitting a specific control signal from the control unit 20 to the active fiber. The incorporation of the active fiber 18 in the textile material of the tube structure 12 provides for correspondence between the shape of the active fiber and the shape of the portion of the tube structure which adjoins the active fiber. Consequently, a change in the shape of the active fiber 18 produces a corresponding change in the shape of the adjoining portion of the tube structure 12.

Incorporating more than one active fiber 18 in the tube structure 12 increases the portion of the tube structure 12 the shape of which corresponds to the shape of the active fibers. The active fibers 18 may be incorporated in the tube structure 12 by weaving, braiding or knitting the active fibers in the textile material of the tube structure.

The incorporation of the active fibers 18 in the tube structure 12 may provide a textile stent structure in which the active fibers may be changed to a shape and have sufficient strength to provide a stent to the tube structure 12. Such a textile tube structure may have a variable shape which may be controlled to have a lower profile for insertion into the body of the patient and, upon reaching the desired location in the body, be expanded transversely to the size for use within the body. Additionally, such expansion may be controlled to various degrees providing for customizing of the vascular graft 10 for specific patients. The electrical coupling between the active fiber 18 and control unit 20 may provide for the continuous adjustment of the shape of the active fibers 18 and the adjoining portions of the tube structure 12.

In an alternative embodiment of the vascular graft 10, the physical characteristic of the active fiber 18 which corresponds to the control signal is the response of the active fiber 18 to stimuli. Consequently, the control signal generated by the active fiber 18 is indicative of the response of the active fiber which is indicative of the stimuli to which the active fiber is exposed. Such stimuli may include changes in morphology and permeability of the active fiber 18. The active fiber 18 may respond to stimuli by stiffening or relaxing. For example, the active fiber 18 may be incorporated in an A/V (arterial/venous) graft. Such an active fiber 18 may relax during the dialysis procedure so that a blunt needle may be used to separate the fibers of the graft for blood access. The use of such a blunt needle would obviate the use of a sharp needle which may cut the fibers of the graft which may shorten the life thereof. Conversely, the one or more active fibers 18 may become rigid to provide a rigid window of access for the needle. Also, the active fiber 18 may detect stimuli by being responsive to a change in electrical resistance, a change in tensile load, a break in an electrical connection, a change in pressure, or an intentional use of a small current through the skin.

The incorporation of the active fiber 18 in the tube structure 12 may provide for the active fiber to be on the inner surface 14 such that the active fiber is exposed to the interior of the tube structure. Consequently, the control signal generated by the active fiber 18 provides an indication of the stimuli within the tube structure 12. Alternatively, the incorporation of the active fiber 18 in the tube structure 12 may provide for the active fiber to be on the outer surface 16 such that the active fiber is exposed to the exterior of the tube structure. Consequently, the control signal generated by the active fiber 18 provides an indication of the stimuli outside of the tube structure 12. Also, the active fiber 18 may extend through the textile material of the tube structure 12 to both the inner and outer surfaces 14, 16 such that portions of the active fiber are exposed to both the interior and exterior of the tube structure. Consequently, the control signal generated by the active fiber 18 provides an indication of the stimuli both within and outside of the tube structure 12.

The transmission of the control signal to the control unit 20 may be initiated by the active fiber 18, or be responsive to a signal received by the active fiber from the control unit intended to prompt the transmission of the control signal by the active fiber to the control unit. The electrical coupling between the active fiber 18 and control unit 20 may provide for the continuous monitoring of the response of the active fiber to the stimuli.

An embodiment of the vascular graft 10 which indicates stimuli directed thereto includes an active fiber 18 having a fiber optic element which responds to optical signals received by the fiber optic element. The response of the fiber optic element to the optical signals is the physical characteristic of the active fiber 18 to which the control signal corresponds. Consequently, the control signal provides an indication of the optical signals to the electrical control unit 20. The control unit 20 processes the control signal to generate a visual image corresponding to the control signal. As a result, a visual image of the region adjacent to the active fiber 18 in vivo may be provided by the control unit 20 which is outside of the body of the patient.

The incorporation of the active fiber 18 in the tube structure 12 may provide for the active fiber to be on the inner surface 14 such that the fiber optic element is exposed to the interior of the tube structure. Consequently, the visual image generated by the control unit 20 provides a view of the region within the tube structure 12. Alternatively, the incorporation of the active fiber 18 in the tube structure 12 may provide for the active fiber to be on the outer surface 16 such that the fiber optic element is exposed to the exterior of the tube structure. Consequently, the visual image generated by the control unit 20 provides a view of the region outside of the tube structure 12. Also, the active fiber 18 may extend through the textile material of the tube structure 12 to both the inner and outer surfaces 14, 16 such that portions of the fiber optic element are exposed to both the interior and exterior of the tube structure. Consequently, the visual image generated by the control unit 20 provides a view of regions both within and outside of the tube structure 12.

Figure 2:
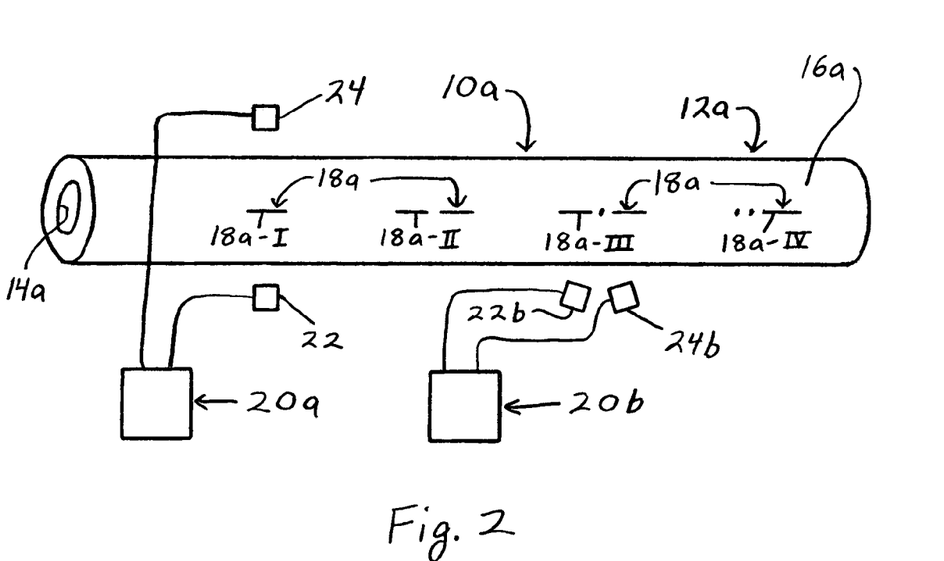
FIG. 2 is a side elevation view in schematic of an alternative second embodiment of the vascular graft of FIG. 1, the electrical control unit being shown as having a signal generator and receiver.

In an alternative embodiment of the vascular graft 10a shown in FIG. 2, the physical characteristic of the active fiber 18a which corresponds to the control signal is the degree of transmission through the active fiber of an identifier signal directed thereto. The vascular graft 10a includes a tube structure 12a. In these and other respects, the vascular graft 10a corresponds to the vascular graft 10. Accordingly, parts illustrated in FIG. 2 which correspond to parts illustrated in FIG. 1 have, in FIG. 2, the same reference numeral as in FIG. 1 with the addition of the suffix "a". The tube structure 12a is partially or completely transparent to the identifier signal.

The electrical control unit 20a has a signal generator 22 for directing the identifier signal to the active fiber 18a. The signal generator 22 may be prompted to generate the identifier signal by an electrical signal received by the signal generator from the control unit 20a. Alternatively, the signal generator 22 may initiate the generation of the identifier signal.

The control unit 20a has a signal receiver 24 for sensing the condition of the identifier signal following contact thereof with the tube structure 12a. The signal generator and receiver 22, 24 have approximately the same longitudinal position along the tube structure 12a. The signal generator and receiver 22, 24 face transversely opposed portions of the outer surface 16, as shown in FIG. 2, such that the identifier signal is directed by the signal generator toward the surface of the signal receiver which faces the outer surface 16a.

The sensing of the identifier signal by the signal receiver 24 causes the signal receiver to provide a control signal for transmission to the control unit 20a. The control signal provides information to the control unit 20a relating to the location of the active fiber 18a relative to the location of the signal generator and receiver 22, 24 since the sensing indicates the presence or absence of the active fiber and the portion of the tube structure 12a which adjoins the active fiber. This enables the location of the portion of the tube structure 12a containing the active fiber 18a in vivo by positioning the signal generator and receiver 22, 24 relative to the body such that the identifier signal is sensed by the signal receiver 24.

The signal receiver 24 may be prompted to transmit the control signal to the control unit 20a by an electrical signal received by the signal receiver from the control unit. Alternatively, the signal receiver 24 may initiate the transmission of the control signal to the control unit 20a.

In one embodiment of the vascular graft 10a, the tube structure 12a is either partially or completely transparent to the identifier signal and the active fiber 18a is either partially or completely opaque to the identifier signal. This degree of transmission of the identifier signal by the active fiber 18a is the physical characteristic thereof to which the control signal corresponds. Consequently, the sensing by the signal receiver 24, after emission of the identifier signal from the signal generator 22, provides an indication of whether the identifier signal contacted the active fiber 18a. For example, the sensing by the signal receiver 24 of the identifier signal, in the same condition as the condition of the identifier signal emitted from the signal generator 22, indicates that the identifier signal did not contact the active fiber 18a. This indicates the absence of the active fiber 18a from the path of the identifier signal which provides information regarding the location of the portion of the tube structure 12a which contains the active fiber. Alternatively, an identifier signal not being sensed or the sensing of an incomplete identifier signal by the signal receiver 24, after emission of the identifier signal from the signal generator 22, indicates that all or part of the identifier signal contacted the active fiber 18a which obstructed transmission of the entire identifier signal to the signal receiver 24. This indicates the intersection of the active fiber 18a with the path of the identifier signal which indicates that the location of the portion of the tube structure 12a containing the active fiber 18a faces the signal receiver 24.

In an alternative embodiment of the vascular graft 10a, the active fiber 18a provides interference to an identifier signal which contacts the active fiber such that the identifier signal is altered. This degree of transmission of the identifier signal by the active fiber 18a is the physical characteristic thereof to which the control signal corresponds. The altered identifier signal may be sensed by the signal receiver 24 to provide an indication of the intersection between the active fiber 18a and path of the identifier signal. This indicates the location of the portion of the tube structure 12a containing the active fiber 18a relative to the signal receiver 24.

In an alternative embodiment of the vascular graft 10a, the active fiber 18a reflects the identifier signal directed to the active fiber. The active fiber 18a may reflect all or a portion of the identifier signal. This degree of transmission of the identifier signal by the active fiber 18a is the physical characteristic thereof to which the control signal corresponds. Such an active fiber 18a is used with a control unit 20b which has a signal generator and receiver 22b, 24b, as shown in FIG. 2. In these and other respects, the control unit 20b corresponds to the control unit 20a. Accordingly, parts of the control unit 20b which correspond to parts of the control unit 20a illustrated in FIG. 2 have the same reference numeral with the addition of the suffix "b".

The control unit 20b provides for the signal generator and receiver 22b, 24b being adjacent to one another and facing the same region of the outer surface 16a. The surfaces of the signal generator and receiver 22b, 24b which face the outer surface 16a may be inclined, as shown in FIG. 2, to provide for the direction of the identifier signal by the signal generator 22b toward the outer surface 16a such that the reflection of the identifier signal from the active fiber 18a is directed toward the signal receiver 24b.

The reflected identifier signal may be sensed by the signal receiver 24b to provide an indication of the presence or absence of the active fiber 18a and the adjoining portion of the tube structure 12a in the path of the identifier signal. For example, the sensing of all or a portion of the identifier signal by the signal receiver 24b after emission from the signal generator 22b indicates that the identifier signal was reflected by the active fiber 18a in the direction of the signal receiver. This indicates the presence of the active fiber 18a in the path of the identifier signal, which indicates the location of the portion of the tube structure 12a containing the active fiber 18a as facing the signal generator and receiver 22b, 24b. An identifier signal not being sensed by the signal receiver 24b after emission of the identifier signal from the signal generator 22b indicates that the identifier signal was not reflected by the active fiber 18a in the direction of the signal receiver. This indicates the absence of the active fiber 18a from the path of the identifier signal which provides information regarding the location of the portion of the tube structure 12a which contains the active fiber.

The active fibers 18a may have various configurations as shown in FIG. 2. The active fibers 18a-I, 18a-II, 18a-III, 18a-IV include different numbers and longitudinal dimensions of fibers. Consequently, the effects on the identifier signal from contact with the respective active fibers 18a-I, 18a-II, 18a-III, 18a-IV are different. These differences may be sensed by the signal receivers 24, 24b which provides the control units 20a, 20b with an indication as to which of the active fibers 18a-I, 18a-II, 18a-III, 18a-IV has been contacted by the identifier signal. As a result, the sensing of the identifier signal by the signal receivers 24, 24b provides an indication of the intersection between the identifier signal and a specific one of the active fibers 18a-I, 18a-II, 18a-III, 18a-IV, which indicates that the location thereof and the adjoining portion of the tube structure 12a faces the signal receiver 24, 24b. This provides more specific information regarding the location of the vascular graft 10a within the body of a patient.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A vascular graft for use with an electrical control unit, said vascular graft comprising:
   a tube structure formed of a textile material having an inner surface and outer surface; and
   an active fiber extending through said textile material to said inner surface and outer surface, said active fiber providing electrical coupling thereof to the electrical control unit to provide for transmission of a control signal between said active fiber and the control unit, said active fiber having at least one physical characteristic which is variable and corresponds to the control signal to provide communication between said active fiber and the electrical control unit relating to said physical characteristic, said extension of said active fiber to said inner surface and outer surface providing for said control signal to indicate said physical characteristic on said inner surface and outer surface.

2. A vascular graft according to claim 1, wherein said active fiber is formed such that said physical characteristic is in continuous correspondence with said control signal, said transmission of said control signal between said active fiber and the electrical control unit being continuous to provide for continuous communication between said active fiber and the electrical control unit.

3. A vascular graft according to claim 1, wherein said active fiber provides for said physical characteristic comprising a temperature of said active fiber, said control signal being indicative of the temperature such that said electrical coupling of said active fiber to the electrical control unit provides an indication of the temperature to the electrical control unit.

4. A vascular graft according to claim 1, wherein said active fiber is formed such that said physical characteristic comprises a response of said active fiber to a pressure exerted on said active fiber by a fluid or gas to which said active fiber is exposed, said control signal being indicative of said response such that said electrical coupling of said active fiber to the electrical control unit provides an indication of the pressure to the electrical control unit.

5. A vascular graft according to claim 4, wherein said active fiber comprises a pressure transducer.

6. A vascular graft according to claim 1, wherein said active fiber is formed such that said physical characteristic comprises a longitudinal dimension of at least a portion of said active fiber, said control signal being indicative of said longitudinal dimension such that said electrical coupling of said active fiber to the electrical control unit provides an indication of said longitudinal dimension to the electrical control unit.

7. A vascular graft according to claim 6, wherein said incorporation of said active fiber in said textile material of said tube structure provides for the anchoring of said active fiber to a portion of said tube structure which adjoins said active fiber such that said longitudinal dimension of said active fiber corresponds to a dimension of said portion of said tube structure.

8. A vascular graft according to claim 6, wherein said active fiber comprises a strain gauge.

9. A vascular graft according to claim 6, wherein said tube structure has a transverse plane in which said active fiber is contained such that a change in said dimension indicates a transverse deformation of said tube structure.

10. A vascular graft according to claim 6, wherein said active fiber has opposite ends which are located at longitudinal positions along said tube structure, said longitudinal positions differing from one another such that a change in said dimension indicates a longitudinal deformation of said tube structure.

11. A vascular graft according to claim 1, wherein said active fiber is formed such that said physical characteristic comprises a response of said active fiber to a stimuli to which said active fiber is exposed, said control signal being indicative of said response such that said electrical coupling of said active fiber to the electrical control unit provides an indication of the stimuli to the electrical control unit.

12. A vascular graft according to claim 11, wherein said active fiber comprises a fiber optic element such that said response of said active fiber comprises the response of said active fiber to optical signals received by said fiber optic element, said response providing an indication of the optical signals to the electrical control unit.

13. A vascular graft according to claim 1, wherein said active fiber is formed such that said physical characteristic comprises a degree of transmission of an identifier signal directed to said active fiber, said tube structure being partially or completely transparent to the identifier signal, the electrical control unit having a signal generator for directing the identifier signal to said active fiber, the electrical control unit having a signal receiver for sensing the condition of the identifier signal following contact thereof with said tube structure, the sensing by the signal receiver indicating whether the identifier signal contacted said active fiber which provides information relating to the location of said active fiber relative to the signal generator and receiver.

14. A vascular graft for use with an electrical control unit, said vascular graft comprising:
   a tube structure formed of a textile material; and
   an active fiber incorporated in said textile material, said active fiber providing electrical coupling thereof to the electrical control unit to provide for transmission of a control signal between said active fiber and the control unit, said active fiber having at least one physical characteristic which is variable and corresponds to the control signal to provide communication between said active fiber and the electrical control unit relating to said physical characteristic,
   wherein said active fiber provides for said physical characteristic comprising a temperature of said active fiber, said control signal being indicative of the temperature such that said electrical coupling of said active fiber to the electrical control unit provides an indication of the temperature to the electrical control unit,
   said active fiber comprising a thermocouple.

15. A vascular graft for use with an electrical control unit, said vascular graft comprising:
   a tube structure formed of a textile material; and
   an active fiber incorporated in said textile material, said active fiber providing electrical coupling thereof to the electrical control unit to provide for transmission of a control signal between said active fiber and the control unit, said active fiber having at least one physical characteristic which is variable and corresponds to the control signal to provide communication between said active fiber and the electrical control unit relating to said physical characteristic,
   wherein said active fiber provides for said physical characteristic comprising a temperature of said active fiber, said control signal being indicative of the temperature such that said electrical coupling of said active fiber to the electrical control unit provides an indication of the temperature to the electrical control unit, said incorporation of said active fiber in said textile material of said tube structure providing for thermal conductivity between said active fiber and a portion of said tube structure which adjoins said active fiber such that said temperature of said active fiber corresponds to a temperature of said portion of said tube structure.

16. A vascular graft for use with an electrical control unit, said vascular graft comprising:
   a tube structure formed of a textile material; and
   an active fiber incorporated in said textile material, said active fiber providing electrical coupling thereof to the electrical control unit to provide for transmission of a control signal between said active fiber and the control unit, said active fiber having a physical hardness which is variable and corresponds to said control signal such that said electrical coupling of said active fiber to the electrical control unit provides for variation of said physical hardness by adjustment of said control signal by the electrical control unit.

17. A vascular graft according to claim 16, wherein said adjustment of said control signal provides for an increase in said physical hardness.

18. A vascular graft for use with an electrical control unit, said vascular graft comprising:
   a tube structure formed of a textile material; and
   an active fiber incorporated in said textile material, said active fiber providing electrical coupling thereof to the electrical control unit to provide for transmission of a control signal between said active fiber and the control unit, said active fiber having a shape which is variable and corresponds to said control signal such that said electrical coupling of said active fiber to the electrical control unit provides for variation of said shape by adjustment of said control signal by the electrical control unit, said incorporation of said active fiber in said tube structure provides for said variation of said shape of said active fiber to produce a corresponding change in a shape of said tube structure.

19. A vascular graft according to claim 18, wherein said incorporation of said active fiber in said textile material of said tube structure provides for a correspondence between said shape of said active fiber and a shape of a portion of said tube structure which adjoins said active fiber such that a change in said shape of said active fiber produces a corresponding change in said shape of said portion of said tube structure.

20. A vascular graft for use with an electrical control unit, said vascular graft comprising:
   a tube structure formed of a textile material; and
   an active fiber incorporated in said textile material, said active fiber providing electrical coupling thereof to the electrical control unit to provide for transmission of a control signal between said active fiber and the control unit, said active fiber having at least one physical characteristic which is variable and corresponds to the control signal to provide communication between said active fiber and the electrical control unit relating to said physical characteristic,
   wherein said active fiber is formed such that said physical characteristic comprises a degree of transmission of an identifier signal directed to said active fiber, said tube structure being partially or completely transparent to the identifier signal, the electrical control unit having a signal generator for directing the identifier signal to said active fiber, the electrical control unit having a signal receiver for sensing the condition of the identifier signal following contact thereof with said tube structure, the sensing by the signal receiver indicating whether the identifier signal contacted said active fiber which provides information relating to the location of said active fiber relative to the signal generator and receiver,
   said physical characteristic comprising an opacity to the identifier signal directed to said active fiber such that transmission of the identifier signal through said active fiber is obstructed.

21. A vascular graft for use with an electrical control unit, said vascular graft comprising:
   a tube structure formed of a textile material; and
   an active fiber incorporated in said textile material, said active fiber providing electrical coupling thereof to the electrical control unit to provide for transmission of a control signal between said active fiber and the control unit, said active fiber having at least one physical characteristic which is variable and corresponds to the control signal to provide communication between said active fiber and the electrical control unit relating to said physical characteristic,
   wherein said active fiber is formed such that said physical characteristic comprises a degree of transmission of an identifier signal directed to said active fiber, said tube structure being partially or completely transparent to the identifier signal, the electrical control unit having a signal generator for directing the identifier signal to said active fiber, the electrical control unit having a signal receiver for sensing the condition of the identifier signal following contact thereof with said tube structure, the sensing by the signal receiver indicating whether the identifier signal contacted said active fiber which provides information relating to the location of said active fiber relative to the signal generator and receiver,
   said physical characteristic comprising interference with the identifier signal directed to said active fiber such that the identifier signal is altered by contact with said active fiber.

22. A vascular graft for use with an electrical control unit, said vascular graft comprising:
   a tube structure formed of a textile material; and
   an active fiber incorporated in said textile material, said active fiber providing electrical coupling thereof to the electrical control unit to provide for transmission of a control signal between said active fiber and the control unit, said active fiber having at least one physical characteristic which is variable and corresponds to the control signal to provide communication between said active fiber and the electrical control unit relating to said physical characteristic,
   wherein said active fiber is formed such that said physical characteristic comprises a degree of transmission of an identifier signal directed to said active fiber, said tube structure being partially or completely transparent to the identifier signal, the electrical control unit having a signal generator for directing the identifier signal to said active fiber, the electrical control unit having a signal receiver for sensing the condition of the identifier signal following contact thereof with said tube structure, the sensing by the signal receiver indicating whether the identifier signal contacted said active fiber which provides information relating to the location of said active fiber relative to the signal generator and receiver, said physical characteristic comprising a reluctance to the identifier signal directed to said active fiber such that the identifier signal is reflected from said active fiber.

23. A vascular graft for use with an electrical control unit, said vascular graft comprising:

a tube structure formed of a textile material; and an active fiber incorporated in said textile material, said active fiber providing electrical coupling thereof to the electrical control unit to provide for transmission of a control signal between said active fiber and the control unit, said active fiber having at least one physical characteristic which is variable and corresponds to the control signal to provide communication between said active fiber and the electrical control unit relating to said physical characteristic;

said vascular graft further comprising a plurality of active fibers incorporated in said textile material, each said active fiber providing electrical coupling thereof to the electrical control unit to provide for transmission of a control signal between said active fibers and the control unit, said active fibers having at least one physical characteristic which is variable and corresponds to the control signal to provide communication between said active fibers and the electrical control unit relating to said physical characteristic.

* * * * *